(12) United States Patent
Cerda et al.

(10) Patent No.: US 7,951,608 B2
(45) Date of Patent: May 31, 2011

(54) DETECTING SUCCINYLACETONE

(75) Inventors: Blas Cerda, Milford, MA (US); Alex Cherkasskiy, West Roxbury, MA (US); Yijun Li, Worcester, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 758 days.

(21) Appl. No.: 11/744,789

(22) Filed: May 4, 2007

(65) Prior Publication Data

US 2008/0274563 A1 Nov. 6, 2008

(51) Int. Cl.
*G01N 1/00* (2006.01)
*G01N 24/00* (2006.01)
*B01L 11/00* (2006.01)

(52) U.S. Cl. ......... 436/173; 436/178; 436/177; 422/430

(58) Field of Classification Search ................. 436/173, 436/178, 177; 422/50, 61, 430
See application file for complete search history.

(56) References Cited

U.S. PATENT DOCUMENTS

| 7,195,751 | B2 | 3/2007 | Pappin et al. |
| 2005/0197341 | A1 | 9/2005 | Woolf et al. |
| 2007/0004045 | A1 | 1/2007 | Xu et al. |

OTHER PUBLICATIONS

Chace et al., "Electrospray Tandem Mass Spectrometry for Analysis of Acylcarnitines in Dried Postmortem Blood Specimens Collected at Autopsy from Infants with Unexplained Cause of Death," *Clin. Chem.*, 2001, 47(7):1166-1182.

Rashed et al., "Screening blood spots for inborn errors of metabolism by electrospray tandem mass spectrometry with a microplate batch process and a computer algorithm for automated flagging of abnormal profiles," *Clin. Chem.*, 1997, 43(7):1129-1141.

Sander et al., "Newborn Screening for Hepatorenal Tyrosinemia: Tandem Mass Spectrometric Quantification of Succinylacetone," *Clin. Chem.*, 2006, 52(3):482-487.

Schulze et al., "Expanded Newborn Screening for Inborn Errors of Metabolism by Electrospray Ionization-Tandem Mass Spectrometry: Results, Outcome, and Implications," *Pediatrics*, 2003, 111(6):1399-1406.

Zytkovicz et al., "Tandem Mass Spectrometric Analysis for Amino, Organic, and Fatty Acid Disorders in Newborn Dried Blood Spots: A Two-Year Summary from the New England Newborn Screening Program," *Clin. Chem.*, 2001, 47(11):1945-1955.

Al-Dirbashi et al., "Determination of succinylacetone in dried blood spots and liquid urine as dansylhydrazone by liquid chromatography tandem mass spectrometry," *J. Chrom. B Biomed. Sci. Appl.*, 831:274-280 (2006).

Allard et al., "Newborn screening for hepatorenal tyrosinemia by tandem mass spectrometry: analysis of succinylacetone extracted from dried blood spots," Clin. Biochem., 37:1010-15 (2004).

Cyr et al., "A GC/MS validated method for the nanomolar range determination of succinylacetone in amniotic fluid and plasma: an analytical tool for tyrosinemia type I," J. Chrom. B Biomed. Sci. Appl., 832:24-29 (2006).

Jakobs et al., "Stable isotope dilution analysis of succinylacetone using electron capture negative ion mass fragmentography: an accurate approach to the pre-and neonatal diagnosis of hereditary tyrosinemia type I," Clin. Chim. Acta, 171:223-231 (1988).

La Marca et al., "The inclusion of succinylacetone as marker for tyrosinemia type I in expanded newborn screening programs," Rapid Commun. Mass Spectrom., 22:812-818 (2008).

(Continued)

*Primary Examiner* — Walter D Griffin
*Assistant Examiner* — Christine T Mui
(74) *Attorney, Agent, or Firm* — Fish & Richardson P.C.

(57) ABSTRACT

This invention relates, inter alia, to detecting and/or measuring succinylacetone and one or more additional biological analytes using mass spectrometry.

42 Claims, 9 Drawing Sheets

OTHER PUBLICATIONS

Magera et al., "Quantitative determination of succinylacetone in dried blood spots for newborn screening of tyrosinemia type I," Mol. Genet. Metabl., 88:16-21 (2006).

Rashed et al., "Tandem mass spectrometric assay of succinylacetone in urine for the diagnosis of hepatorenal tyrosinemia," Anal. Biochem., 339:310-317 (2005).

Sapp et al., "Expanded newborn screening by tandem mass spectrometry: considerations on its simplification and potential further expansion," Dec. 19, 2007, retrieved from the internet: URL:http://las.perkinelmer.com/Content/Relatedmaterials/Posters/SPS_APHL2007NeoBase.pdf [retrieved on Aug. 11, 2010].

Schierbeek et al., "Determination of succinylacetone and succinylacetoacetate in physiological samples as the common product 5-3 methyl-3-5-isoxazole propionic acid using an isotope dilution method and mass spectrometry," Clin. Chim. Acta, 184:243-250 (1989).

Turgeon et al., "Combined newborn screening for succinylacetone, amino acids, and acylcarnitines in dried blood spots," Clin. Chem., 54:657-664 (2008).

Supplementary European Search Report for EP 08 75 5064, dated Oct. 25, 2010.

Note: the Succinylacetone region is magnified 5X

DETECTING SUCCINYLACETONE

BACKGROUND

Mass spectrometry is useful for detecting and measuring a wide variety of metabolites, the presence or amount of which can be indicative of certain conditions or disorders. Thus, mass spectrometry can be used, e.g., to diagnose numerous metabolic disorders associated with altered levels of metabolites. One such metabolic disorder is hereditary tyrosinemia, Type I (HT1), which is caused by a deficiency of fumarylacetoacetate hydrolase (FAH) and is associated with increased levels of tyrosine and succinylacetone. HT1 is a childhood disorder that causes liver failure, painful neurological crises, rickets, and hepatocarcinoma. If untreated, death typically occurs at less than 2 years of age, with some chronic forms allowing survival to 12 years of age. It is now possible to treat HT1 with NTBC (or Nitisinone), if treatment is initiated early in life. Thus, there is a major incentive to identify HT1 affected patients by newborn screening or even prenatal screening.

SUMMARY

Succinylacetone is the primary marker for the early detection of HT1. However, succinylacetone is a very reactive ketone that forms conjugates with proteins. The methods described herein can be used to extract succinylacetone from a sample under conditions that permit concurrently extracting other metabolites, such as amino acids, free carnitine, or acylcarnitines. For example, harsh extractions conditions (such as extreme acidity and high temperature) can be avoided.

The methods described herein can be used to detect and/or measure succinylacetone and one or more additional biological analytes using mass spectrometry (e.g., tandem mass spectrometry). Such methods are useful in diagnosis and for generating metabolic profiles for the detection/diagnosis of metabolic disorders such as amino acidopathies (e.g., tyrosinemia type I).

In one aspect, the disclosure provides a method for extraction. The method includes the steps of: contacting a sample with an extraction solution, the extraction solution comprising a C1-3 linear or branched chain monoalcohol and a strong base, wherein contacting the sample with the extraction solution yields an extract comprising: (i) derivatized succinylacetone, (ii) one or more amino acids, (iii) free carnitine, (iv) one or more acylcarnitines, or (iv) derivatized forms of any of (ii), (iii), or (iv) from the sample, and wherein the concentration of the derivatized succinylacetone in the extract reflects the concentration of succinylacetone in the sample, and wherein the concentrations of the one or more amino acids, free carnitine, one or more acylcarnitines, or derivatized forms thereof in the extract reflect their respective concentrations in the sample. The method can also include the step of after contacting the sample with the extraction solution, analyzing the sample using tandem mass spectrometry. The contacting can derivative at least one succinylacetone molecule to 3-(5-methyl-1H-pyrazol-3-yl) proprionic acid (MPP). The C1-3 linear or branched chain monoalcohol cars be methanol, ethanol, propanol, or isopropanol. The strong base can be hydrazine, a modified hydrazine (e.g., acyl-hydrazines, aryl-hydrazines, alkyl-hydrazines, Girard-P and Girard-T reagents), or hydroxylamine.

In some embodiments, the sample can be a biological sample such as a dried blood spot. The sample can be one obtained from a newborn human. The sample can be one obtained from a subject suspected of, or a risk of developing, a metabolic disorder such as tyrosinemia type I.

In some embodiments, the extraction solution can contain water, an organic acid, and/or one or more internal standards. For example, the extraction solution can contain between about 5% to about 30% water or between about 20% to about 25% water. The organic acid can be oxalic acid, e.g., at a concentration of about 5 mM. The internal standards can include at least one heavy atom isotope such as $^2$H, $^{15}$N, or $^{13}$C. One or more of the internal standards can be, or contain, succinylacetone, an amino acid, free carnitine, an acylcarnitine, or derivatized form of any of the aforementioned.

In some embodiments, the method can include the steps of after contacting the sample with the extraction solution, evaporating the sample resulting in a first evaporated sample. The method can further include the steps after evaporating the sample, contacting the first evaporated sample with an alkyl alcohol solution comprising an alkyl alcohol and an acid. The method can further include the steps of: after contacting the sample with the alkyl alcohol solution, evaporating the solution resulting in a second evaporated sample and/or reconstituting the second evaporated sample. Reconstituting the second evaporated sample can include contacting the second evaporated sample with a solvent. The alkyl alcohol can be methanol, ethanol, propanol, isopropanol n-butanol, t-butanol, or pentanol. The acid can be hydrochloric acid (HCl). The solvent can include acetonitrile, isopropanol, or a mixture of water with isopropanol or acetonitrile.

In another aspect, the disclosure provides a method for extraction, which method includes the steps of: contacting a sample with an extraction solution, the extraction solution comprising a C1-3 linear or branched chain monoalcohol and a strong base, wherein contacting the sample with the extraction solution yields an extract comprising (i) a derivatized biologically active ketone, (ii) one or more amino acids, (iii) free carnitine, (iv) one or more acylcarnitines, and/or (v) derivatized forms of any of (ii), (iii), or (iv) from the sample, and wherein the concentration of the derivatized biologically active ketone in the extract reflects the concentration of the biologically active ketone in the sample, and wherein the concentrations of the one or more amino acids, free carnitine, one or more acylcarnitines, or derivatized forms thereof in the extract reflect their respective concentrations in the sample. The C1-3 linear or branched chain monoalcohol can be methanol, ethanol, propanol, or isopropanol. The biologically active ketone can be, e.g., succinylacetone or a steroid. Steroids include, but are not limited to, testosterone dehydroepiandrosterone (DHEA), dehydroepiandrosterone sulfate, adrostenedione, 17-hydroxyprogesterone (17-OHP), 17-hydroxy pregnenolone, cortisol, 11-deoxycortisol, corticosterone, aldosterone, estradiol, 18-OH corticosterone, pregnenolone, progesterone, cortisone, terta-hydrocortisol, 11-deoxycorticosterone, creatinine, 17-Ketosteroids, cholesterol, vitamin B, or vitamin A. The strong base can be any of the strong bases described herein. The extraction solution can also include water.

In another aspect, the disclosure features a method for detecting succinylacetone. The method includes the steps of: contacting a sample with an extraction solution comprising a C1-3 linear or branched monoalcohol and a strong base; derivatizing succinylacetone in the sample; and evaluating the derivatized succinylacetone in the derivatized sample using tandem mass spectrometry. The derivatized form of succinylacetone can be succinylacetone to 3-(5-methy-1H-pyrazol-3-yl) proprionic acid (MPP). The strong base can be any described herein.

In another aspect, the disclosure provides a method for detecting succinylacetone, which method includes the steps of contacting a sample with an extraction solution comprising a C1-3 linear or branched monoalcohol and hydrazine; derivatizing succinylacetone to 3-(5-methyl-1H-pyrazol-3-yl) proprionic acid (MPP) in the sample; and evaluating MPP in the derivatized sample using tandem mass spectrometry. The method can also include evaluating the sample for one or more additional analytes (e.g., any of the additional analytes described herein) with MPP in the same sample injection. The C1-3 linear or branched chain monoalcohol can be methanol, ethanol, propanol, or isopropanol.

In another aspect, the disclosure provides a method for detecting succinylacetone. The method can include the steps of contacting a sample with an extraction solution containing an organic solvent under conditions that do not substantially fix proteins; derivatizing succinylacetone to 3-(5-methyl-1H-pyrazol-3-yl) proprionic acid (MPP) in the sample; and evaluating MPP and an additional analyte (or derivative thereof) in the derivatized sample using tandem mass spectrometry. The extraction solution can contain about 5% water. The extraction solution can contain about 85% of a C1-3 linear or branched monoalcohol such as methanol, ethanol, propanol, or isopropanol. Succinylacetone can be derivatized with hydrazine or derivatized hydrazine.

In some embodiments, the method can include the steps of determining whether a subject, from whom the sample was derived, has, or is at risk of developing, hereditary tyrosinemia type I, based on the detection of succinylacetone in the sample. After determining that a subject has, or is at risk of developing, hereditary tyrosinemia type I, the method can include administering to the subject an inhibitor of 4-hydroxyphenylpyruvate dioxygenase.

In yet another aspect, the disclosure features a method for detecting a biologically active ketone. The method can include the steps of: contacting a sample with an extraction solution comprising a C1-3 linear or branched monoalcohol and a strong base; derivatizing a biologically active ketone in the sample; and evaluating the derivatized biologically active ketone in the derivatized sample using tandem mass spectrometry. The biologically active ketone can be succinylacetone or a steroid such as any of the steroids described herein. The C1-3 linear or branched chain monoalcohol can be methanol ethanol, propanol or isopropanol. The extraction solution can also include water.

In some embodiments of any of the methods described herein, the sample can be a biological sample such as a dried blood sample (a dried blood spot). The sample can be from a newborn human. The sample can also include at least one heavy atom isotope is included in the sample prior to mass spectroscopic analysis.

In some embodiments of any of the methods described herein, the evaluating can include analyzing derivatized succinylacetone along with one or more additional analytes (e.g., biological analytes such as one or more amino acids, free carnitine, or acylcarnitines) from the sample injection into a tandem mass spectrometer. For example, derivatized succinylacetone can be analyzed along with one or more (e.g., two, three, four, five, six, seven, eight, nine, 10, 11, 12, 15, 18, 20, 22, 25, 28, or 30) additional analytes from the same sample injection (into a tandem mass spectrometer).

In some embodiments of any of the methods described herein, the sample is one that has not been previously extracted.

In some embodiments of any of the methods described herein, contacting the sample with the extraction solution results in the extraction of (i) derivatized succinylacetone (SA) and (ii) one or more amino acids, free carnitine, one or more acylcarnitines, or derivatized forms thereof from the sample without altering the ratios of these analytes present in the sample. For example, an extract obtained from a sample containing SA, tyrosine, and free carnitine at a ratio of approximately 5:1:2 would contain derivatized succinylacetone, tyrosine (or derivatized tyrosine), and free carnitine (or derivatized free carnitine) at a ratio of approximately 5:1:2.

In yet another aspect, the disclosure features a kit for detecting succinylacetone. The kit can include derivatized succinylacetone comprising at least one heavy atom isotope; and instructions for how to detect the derivatized succinylacetone. The kit can also include a strong base such as hydrazine. The strong base can be provided at a concentration of less than about 0.1%. The hydrazine can be hydrazine dihydrochloride. The kit can also include one or more internal standards, each internal standard containing: (i) an amino acid, free carnitine, or an acylcarnitine and (i) at least one heavy atom isotope. The kit can also include at least one dried blood spot comprising a known amount of one or more of succinylacetone, an amino acid, free carnitine, or an acylcarnitine. The derivatized succinylacetone can be 3-(5-methyl-1H-pyrazol-3-yl) proprionic acid (MPP).

In another aspect, the disclosure provides a kit for detecting a biologically active ketone. The kit can include a derivatized biologically active ketone of interest containing at least one heavy isotope atom and instructions for how to detect the derivatized biologically active ketone.

Many mass spectrometers have mass accuracies to high resolution. For example, in the case of a singly charged ion, this range corresponds to 0.6 m/z. Minor variations (e.g., variations in the calibration) in a mass spectrometer may result in ion m/z signals that do not coincide with the ones stated herein, but the m/z signal corresponding to those disclosed can be easily identified and used, e.g., by compensating for offset in calibration.

All publications, patent applications, patents, and other references mentioned herein are incorporated by reference in their entirety.

DETAILED DESCRIPTION

Succinylacetone can be detected by mass spectrometry by modifying succinylacetone in a sample to a more stable form. Disclosed herein are methods and compositions for performing such modifications and for concurrently treating the sample in a manner that allows for the extraction of succinylacetone and other analytes (e.g., amino acids, acylcarnitines, and free carnitine) from a sample in a single step such that the concentrations of succinylacetone and the other analytes in the extract reflect their respective concentrations in the sample. Also disclosed are methods for detecting and/or measuring succinylacetone (derivatized succinylacetone) and one or more additional analytes using mass spectrometry. The methods described, herein can be used, inter alia, for diagnosing one or more metabolic disorders in a subject such as amino acidopathies (e.g., Hereditary tyrosinemia type I) and disorders of organic and fatty acid metabolism or for generating metabolic profiles for such diagnoses (see below).

Methods for Extracting Succinylacetone and Additional Analytes from a Sample

The disclosure features methods for extracting succinylacetone along with one or more additional analytes (e.g., amino acids, acylcarnitines, and free carnitine) from the sample in a single step such that the concentrations of succinylacetone and one or more additional analytes (e.g., amino acids, free carnitine, and acylcarnitines) in the extract reflect their respective concentrations in the sample. Following the extraction, the presence or amount of succinylacetone can be determined along with one or more additional analytes (e.g., free carnitine, acylcarnitines, and amino acids) using mass spectrometry (e.g., tandem mass spectrometry). The methods can include contacting a sample with an extraction solution containing a C1-3 linear or branched chain monoalcohol (e.g., methanol, ethanol, propanol, or isopropanol) and a strong base such as hydrazine, a modified hydrazine (e.g., acyl-hydrazines, aryl-hydrazines, alkyl-hydrazines, Girard-P and Girard-T reagents), or hydroxylamine. The extraction solution can also contain water. Contacting the sample with the extraction solution results in modification (derivatization) of succinylacetone, if present in the sample and the extraction of the modified succinylacetone as well as one or more additional analytes (e.g., free carnitine, acylcarnitines, and amino acids)

Figure 2:
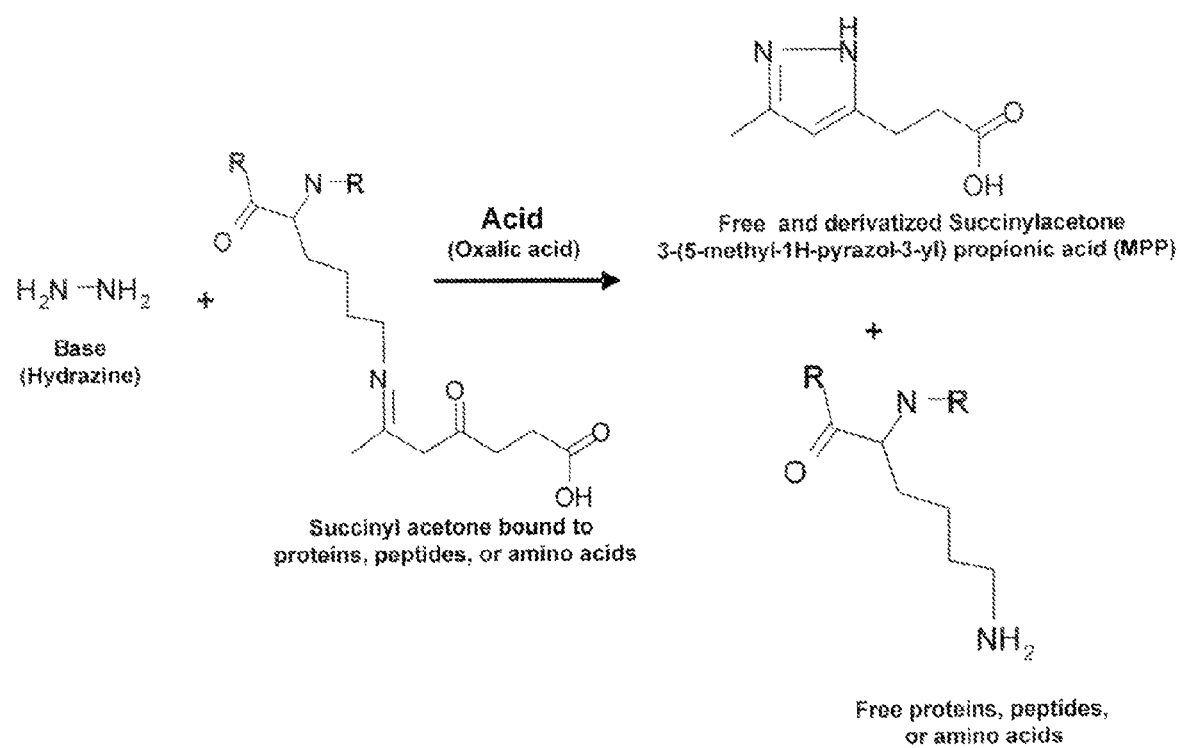
FIG. 2 is a schematic diagram depicting a reaction necessary to extract and derivative succinylacetone from a biological sample.

FIG. 2 depicts an exemplary reaction for extracting succinylacetone from the dried blood spot samples according to the methods described herein. Succinylacetone is a very reactive diketone and thus it reacts rapidly with the side chains of certain amino acids (e.g., free amino acids or constituents of peptides and proteins) in biological fluids such as whole blood. The Schiff base conjugates formed by the reaction between succinylacetone and the amino acid residues are more stable than the free succinylacetone and thus most, if not all, succinylacetone present in blood is in the bound form. To extract (release) succinylacetone along with one or more additional analytes from a sample (e.g., a biological sample such as a blood spot) in a single step, the sample can be contacted with an extraction solution containing a C1-3 linear or branched chain monoalcohol (e.g., methanol, ethanol, propanol, or isopropanol) and a strong base. The strong base can be hydrazine or a modified hydrazine (e.g., acyl-hydrazines, aryl-hydrazines, alkyl-hydrazines, Girard-P and Girard-T reagents) as well as hydroxylamine. The C1-3 linear or branched chain monoalcohol can be, for example, at a concentration of about 70% (e.g., about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%) by volume in the solution. The strong base (e.g., hydrazine, modified hydrazine, or hydroxylamine) can be at a concentration of about 600 μM (e.g., about 200 μM, about 300 μM, about 400 μM, about 500 μM, about 550 μM, about 650 μM, about 700 μM, about 800 μM, about 900 μM, about 1,000 μM, about 1,200 μM, about 1,500 μM, or about 2,000 μM) in the solution.

The extraction solution can also contain water. The water can be, for example, at a concentration of 6-30% (e.g., 7-28%, 8-26%, 10-26%, 14-25%, 18-24%) by volume in the extraction solution. The concentration of water can be such that the extraction solution reconstitutes some of the proteins and peptides while at the same time dissolving other analytes (e.g., acylcarnitines, free carnitine, and amino acids) present in the sample. The extraction solution can also contain an organic acid such as oxalic acid at a concentration of about 3 mM (e.g., about 1 mM, about 2 mM, about 2.5 mM, about 3.5 mM, about 4 mM, about 4.5 mM, or about 5 mM).

Optionally, with the aid of the organic acid (e.g., oxalic acid), which acts as a catalyst, hydrazine releases succinylacetone from the amino acid residues and forms a stable pyrazone ring. The pyrazone formed by the reaction between succinylacetone and hydrazine is the compound called 3-(5-methyl-1H-pyrazol-3-yl)propionic acid (MPP). This compound is more stable than the Schiff bases form by the reaction of succinylacetone with amino acid residues. Therefore, once succinylacetone has reacted with hydrazine, this MPP derivative can be fully extracted along with additional analytes (e.g., amino acids, free carnitine, and acylcarnitines) in a single step. The extracted MPP and additional analytes can then be measured using tandem mass spectrometry. Succinylacetone and other analytes can be evaluated, for example, concurrently using tandem mass spectrometry. The concentration of MPP directly reflects the concentration of succinylacetone in the sample.

Figure 3:
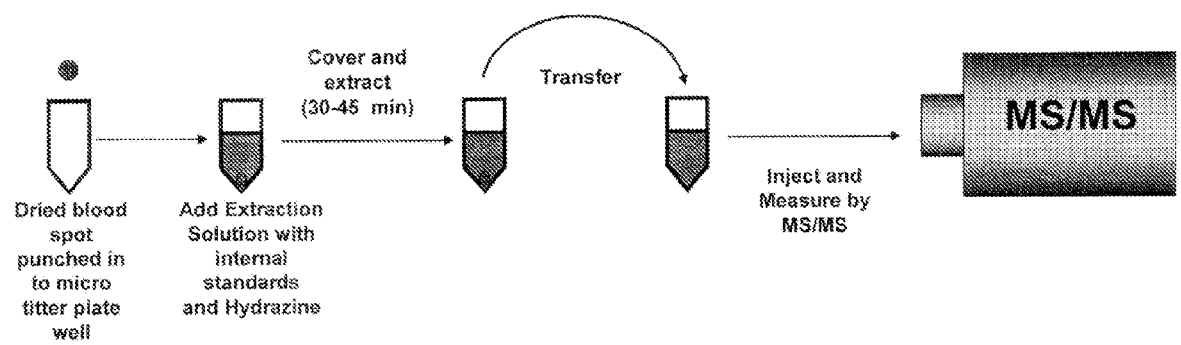
FIG. 3 is a schematic diagram of a method of extracting and derivatizing succinylacetone prior to injection and detection/measurement by tandem mass spectrometry.

FIG. 3 depicts an exemplary method for preparing a sample for mass spectrometric analysis. In this case, a dried blood spot sample obtained from a newborn (or person of any age) can be perforated to generate a small disc that is deposited, e.g., in a well of a microliter plate. To this sample, an extraction solution can be added to extract the analytes in the sample. The extraction solution can comprise a mixture of a C1-3 linear or branched chain monoalcohol and a strong base (the proportions of these two components can vary as described above). The source of hydrazine can be hydrazine hydrate or hydrazine dihydrochloride, or other modified hydrazines (e.g., acyl-hydrazines, aryl-hydrazines, alkyl-hydrazines, Girard-P and Girard-T reagents) or hydroxylamine. The solution can also contain water (see above) with a small percentage of an organic acid (e.g., oxalic acid). This solution can also, optionally, contain one or more internal standards for, e.g., amino acids, free carnitine, acylcarnitines and succinylacetone at known concentrations. The sample mixture can then be incubated for a pre-determined period of time (e.g., about 25 to about 45 minutes (e.g., about 30 to about 45 minutes; about 30 to about 60 minutes; about 30 to about 70 minutes; about 30 to about 90 minutes; about 30 to about 120 minutes; about 35 to about 60 minutes; or about 40 to about 60 minutes) to allow the extraction of amino acids, free carnitine and acylcarnitines as well as the extraction of bound succinylacetone and its concomitant reaction with hydrazine to occur. The extract can then be transferred to an unused well of a micro titer plate and the samples then analyzed by tandem mass spectrometry, optionally, with the aid of a liquid handling device for sample injection. The instrumental settings on the tandem mass spectrometer are then set to detect the respective metabolites of interest (amino acids, acylcarnitines, carnitine, and succinylacetone) as well as their corresponding internal standards in a multiplex fashion.

Figure 4:
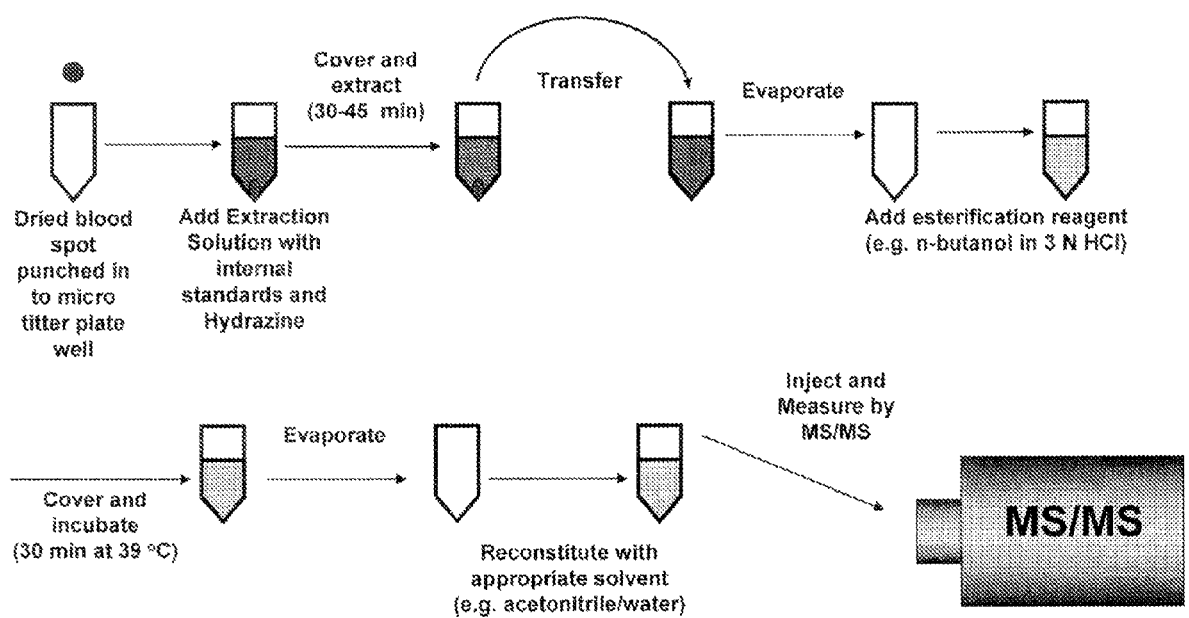
FIG. 4 is a schematic diagram of a method of extracting and derivatizing succinylacetone, and extracting and esterifying additional analytes prior to injection and detection/measurement by tandem mass spectrometry.

It can be advantageous to derivative not only the modified succinylacetone (e.g. MPP), but additional analytes in a sample (e.g. additional analytes such as amino acids, acylcarnitines, and carnitine). Many of the analytes described herein, including succinylacetone, are carboxylic acids; therefore, they are amenable for sample derivatization by esterification. An exemplary method for esterifying multiple analytes in a sample, prior to analysis by mass spectrometry, is depicted in FIG. 4. First, a similar procedure can be performed as above, however, further sample processing can be performed. For example, following the derivatization step with hydrazine, the sample can be evaporated to dryness. The dried sample can then be reconstituted in an acidic solution of an alkyl alcohol. The alcohol can be any alkyl alcohol such as, but not limited to, methanol, ethanol, propanol, n-butanol, tert-butanol, pentanol, or hexanol. This alcohol can be contacted with the sample in combination with a strong, concentrated acid (e.g., hydrochloric acid or sulfuric acid). Such a solution of an alkyl alcohol and an acid can be, for example, butanol in 3N HCl or methanol in 1N HCl. The sample can be incubated in the alkyl alcohol/acid solution for about 30 minutes (e.g., about 20 minutes, about 40 minutes, about 45 minutes, about 50 minutes, about 60 minutes, about 70 minutes, about 80 minutes, about 90 minutes, about 100 minutes, or about 120 minutes) at about 39° C. (e.g., about 30° C., about 35° C., about 36° C., about 37° C., about 40° C., about 42° C., about 50° C., about 55° C., about 60° C., or about 70° C.). Following this incubation, the sample can be evaporated to dryness and then reconstituted in a solvent (e.g., acetonitrile; or acetonitrile and water (e.g., 80% acetonitrile and 20% water), isopropanol (e.g. 80% isopropanol and 20% water) or any other solvent that is amenable for mass spectrometry analysis and that is capable of dissolving esterified organic compounds.

Additional analytes that can be detected and/or measured with derivatized (modified) succinylacetone include, e.g., those listed in Table 1.

TABLE 1

| ANALYTE NAME | ABBREVIATION |
|---|---|
| Ketones | |
| Succinylacetone | SA |
| Amino acids | |
| Alanine | Ala |
| Arginine | Arg |
| Aspartic Acid | Asp |
| Asparagine | Asn |
| Citrulline | Cit |
| Cysteine | Cys |
| Glycine | Gly |
| Glutamine | Gln |
| Glutamic Acid | Glu |
| Histidine | His |
| Leucine (isoleucine, Allo-Isoleucine) | Leu (Ile, Allo-Ile) |
| Lysine | Lys |
| Methionine | Met |
| Ornithine | Orn |
| Phenylalanine | Phe |
| Proline | Pro |
| Serine | Ser |
| Threonine | Thr |
| Tryptophan | Trp |
| Tyrosine | Tyr |
| Valine | Val |
| Carnitines | |
| Free carnitine | C0 |
| Acetylcarnitine | C2 |
| Propionylcarnitine | C3 |
| Malonylcarnitine | C3DC |
| Butyrylcarnitine | C4 |
| 3-Hydroxy-butyrylcarnitine | C4OH |
| Isovalerylcarnitine | C5 |
| Tiglylcarnitine | C5:1 |
| Glutarylcarnitine | C5DC |
| 3-Hydroxy-isovalerylcarnitine | C5OH |
| Hexanoylcernitine | C6 |
| Adipylcarnitine | C6DC |
| Octanoylcernitine | C8 |
| Octenoylcarnitine | C8:1 |
| Decanoylcarnitine | C10 |
| Decenoylcarnitine | C10:1 |
| Decadienoylcarnitine | C10:2 |
| Dodecanoylcarnitine | C12 |
| Dodecenoylcarnitine | C12:1 |
| Tetradecanoylcarnitine (Myristoylcarnitine) | C14 |
| Tetradecenoylcarnitine | C14:1 |
| Tetradecadienoylcarnitine | C14:2 |
| 3-Hydroxy-tetradecanoylcarnitine | C14OH |
| Hexadecanoylcarnitine (palmitoylcarnitine) | C16 |
| Hexadecenoylcarnitine | C16:1 |
| 3-Hydroxy-hexadecanoylcarnitine | C16OH |
| 3-Hydroxy-hexadecenoylcarnitine | C16:1OH |
| Octadecanoylcarnitine (Stearoylcarnitine) | C18 |
| Octadecenoylcarnitine (Oleylcarnitine) | C18:1 |
| Octadecadienoylcarnitine (Linoleylcarnitine) | C18:2 |
| 3-Hydroxy-octadecanoylcarnitine | C18OH |
| 3-Hydroxy-octadecenoylcarnitine | C18:1OH |

Mass Spectrometry

Tandem mass spectrometry can be used to detect and/or measure succinylacetone and one or more additional analytes (e.g., free carnitine, acylcarnitines, and amino acids) in a sample (e.g., a biological sample). In tandem mass spectrometry, two mass analyzers are linked in series via a collision cell. The first mass analyzer (MS-1) is used to select an ion of interest (e.g., an ion of a particular mass-to-charge ratio (m/z)). The selected ions are then transferred to the collision cell where they are fragmented by collisions with an inert gas. This process is called collisionally activated dissociation (CAD). Once the parent (sometimes referred to as precursor) ions have fragmented, the second mass analyzer (MS-2) is used to either scan and detect all of the produced daughter ions or to select and detect particular fragment ions.

Figure 5:
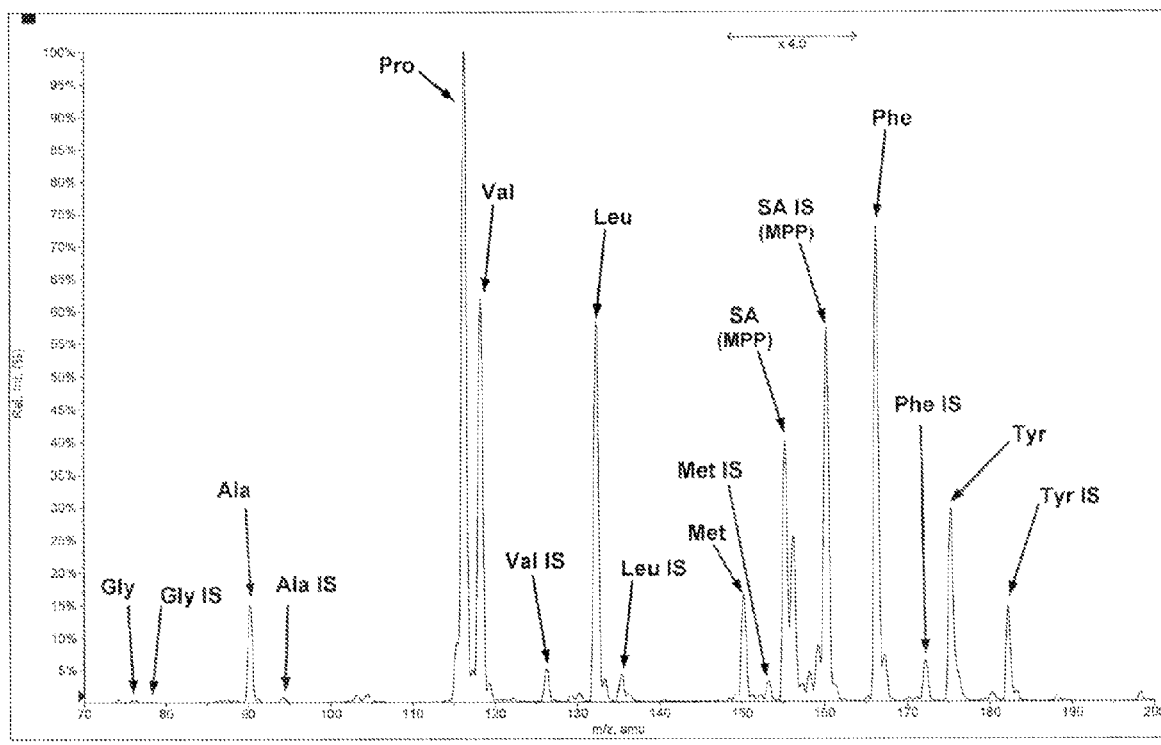
FIG. 5 is a tandem mass spectrum (Neutral loss of 46 scan) acquired using the method depleted in FIG. 3 of derivatized succinylacetone and other non-derivatized amino acids. Amino acids are designated by three-letter code, e.g., alanine is "ala," and the specific mass-to-charge ratio (m/z) signal for a daughter ion of an individual amino acid is indicated by arrow. "IS" refers to internal standard. The X-axis represents the m/z and the Y-axis represents the relative abundance (percentage) of each ion in the sample.

As detailed in the accompanying Examples, tandem mass spectrometry was used to ionize the precursor molecules of derivatized (modified) succinylacetone and several amino acids, fragment the ions, and detect specific peaks that are indicative of the presence of these molecules in the sample. The tandem mass spectrometry detection can be accomplished in a number of ways. In one type of tandem mass spectrometry (commonly performed on triple quadrupole tandem mass spectrometers) ions that fragment to produce common daughter (fragment) ions can be detected as a class by performing a "precursor ion scan" (also called parent ion scan), where by selecting the appropriate mass for the common fragment ion in MS-2 all ion that produce the common fragment ions are detected. This type of scan can be used to detect the acylcarnitines in a sample (precursor ion of m/z 85 scan). In a different form of tandem mass spectrometry, ions that fragment to produce a common neutral loss can be detected as a class by performing a so called neutral loss scan where by setting an appropriate mass offset equal to the common neutral loss between MS-1 and MS-2 all ions that fragment to produce the specified neutral loss are detected. This type of scan is performed to detect amino acids and succinylacetone in a sample (neutral loss of m/z 102 if the analytes in the extracted sample were modified in to butyl esters or neutral loss of m/z 46 if no further analyte modification occurred). FIG. 5 shows a neutral loss scan of m/z 46 were several amino acids and succinylacetone are defected from the same sample. A unique peak corresponding to derivatized succinylacetone is observed at m/z 155, together with several unique peaks corresponding to amino acids. Thus, succinylacetone (derivatized succinylacetone as described herein) can be detected and/or measured along with one or more additional analytes in a single sample in one analysis.

In yet another type of tandem mass spectrometry known as multiple reaction monitoring (MRM), a parent ion of interest is selected in MS-1, fragmented in the collision cell and a specific fragment ion resulting from the collisional activation is selected in MS-2 and finally detected. MS-1 and MS-2 are fixed to respectively select the corresponding parent and fragment ion pairs of interest for a predetermined amount of time (a few milliseconds). This specific parent ion-product ion transition can be considered as one detection channel. If additional analytes need to be detected, additional detection channels with specific mass transitions can be introduced in the experiment. The data from all selected mass transitions (channels) can be acquired sequentially to obtain the desired information. The detection and quantitation of succinylacetone (derivatized succinylacetone in a sample prepared as described herein) in a mixture can be obtained by employing the specific mass transition for each of these compounds as follows: for derivatized succinylacetone: MS-1 fixed to select and transmit the parent ion at m/z 155, MS-2 fixed to select and transmit the specific product ion at m/z 109 (channel 1 or MRM transition 1); and for an amino acid, such as tyrosine: MS-1 fixed to select and transmit the parent ion at m/z 182, MS-2 fixed to select and transmit the specific product ion at m/z 136 (channel 2 or MRM transition 2). These two MRM transitions can be measured sequentially from the same sample for a predetermined amount of time to detect the presence and/or concentration of a mixture of these compounds in such sample.

Stable isotope-labeled internal standards for succinylacetone (derivatized succinylacetone) can be added to a sample, by which quantitation of derivatized succinylacetone, and thus succinylacetone itself, can be performed. Such labeling of derivatized succinylacetone with stable isotopes results in a mass shift, while retaining very similar physicochemical properties between the labeled and unlabeled compounds.

Generally, one or more internal standards can be added at known concentration to a sample to allow for quantitation of the analyte of interest (e.g., succinylacetone). For example, for a sample analyzed using tandem mass spectrometry, the ratio of the signals produced by derivatized succinylacetone (e.g., MPP) and its corresponding internal standard can be used to determine the amounts of this compound in the sample. The internal standard can also be added to distinguish naturally occurring (endogenous) molecules. As above, the internal standards can be prepared in an extraction solution prior to mixing a sample (e.g., a blood sample) and the extraction solution. Alternatively, the internal standards can be added to the mixture at any step in the sample preparation that ensures these internal standards will not be removed from the mixture during the sample processing (e.g. after a liquid-liquid extraction or a solid phase extraction).

Internal standards for an analyte of interest (or other molecules, e.g., biomolecules described herein) detected by a method described herein can be any modification or analog of that analyte molecule that is detectable by mass spectrometry. An internal standard is separately detectable from the molecule based on unique physical characteristics, such as a unique mass or mass-to-charge ratio. A commonly used internal standard for mass spectrometry is a stable isotopically labeled form or chemical derivative of an analyte of interest (e.g., if the analyte was MPP, the internal standard can be an isotopically labeled MPP). For example, stable isotope labeled analogs can be used to quantitate the corresponding analyte of interest using the technique known as isotope dilution mass spectrometry where the analyte and internal standards are processed in the same sample. Internal standards can be designed such that 1) the labeling causes a shift in mass of at least 1 mass unit and 2) that none of the stable isotope labels are located in labile sites to prevent exchange. Labels can be $^2H$ (D), $^{15}N$, $^{13}C$ or $^{18}O$ in any combination. The actual location of the labels on the molecule can vary provided the pre-requisite 2 (above) is satisfied. Moreover, the position of the labels and the potential change in the mass of the fragment ions can also be used to confirm separation of the internal standard and analytes. Examples of potential internal standards useful in the methods described herein include, but are not limited to, an isotopically labeled: derivatized succinylacetone (e.g., 3-(5-methyl-1H-pyrazol-3-yl)propionic acid (MPP)), carnitine, acylcarnitine, or amino acid (e.g., proline, methionine, or tyrosine).

Several types of mass spectrometers are available or can be produced with various configurations, all of which can be useful in the methods described herein. In general, a mass spectrometer has the following major components: a sample inlet, an ion source, a collision cell, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include quadrupole mass filters, time-of-flight mass analyzers (preferably an orthogonal acceleration time-of-flight mass analyzer), ion trap mass filters, magnetic sector analysers, or Fourier Transform Ion Cyclotron Resonance ("FTICR") mass analysers. The collision cell can be, e.g., a quadrupole rod set, a hexapole rod set, or an octopole rod set. The collision cell preferably forms a substantially gas-tight enclosure apart from an ion entrance and ion exit aperture. A collision gas such as helium, argon, nitrogen, air or methane may be introduced into the collision cell.

The specific examples described herein were performed using tandem mass spectrometers (see, e.g., the accompanying Examples).

Samples

Suitable samples for the methods described herein include any biological fluid, cell, tissue, or fraction thereof, that includes biomolecules indicative of a metabolic state (e.g., a metabolic disorder characterized by altered succinylacetone levels such as Hereditary tyrosinemia type I). A sample can be, for example, a specimen obtained from a subject (e.g., a mammal such as a human) or can be derived from such a subject. For example, a sample can be a tissue section obtained by biopsy, or cells that are placed in or adapted to tissue culture. Exemplary samples therefore include cultured fibroblasts, cultured amniotic fluid cells, and chorionic villus sample. A sample can also be a biological fluid specimen such as urine, blood, plasma, serum, saliva, semen, sputum, cerebral spinal fluid, tears, mucus, and the like. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamne tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For use in the methods described herein, a sample can be in a variety of physical states. For example, a sample can be a liquid or solid, can be dissolved or suspended in a liquid, can be in an emulsion or gel, and can be absorbed onto a material. As a non-limiting example, a sample can be a liquid blood sample, liquid serum sample, liquid white blood cell sample, dried blood, serum, or white cell sample, or such a sample absorbed onto a paper or polymer substrate.

Exemplary Applications

The methods described herein can be used to obtain a molecular profile for a sample, e.g., a sample from a subject such as a human. The profile can include information that indicates whether succinylacetone, or succinylacetone and other biological analytes such as amino acids, is present and typically includes information about the presence (either qualitative or quantitative) of succinylacetone (and one or more additional biological analytes).

In some applications of these mass spectrometry methods, metabolic profiles for a subject (e.g., a human) can be obtained. For example, the profiles can include the level of succinylacetone in a subject (e.g., a human patient). Other biomolecules can also be detected, quantitated, and/or evaluated, including, e.g., one or more of an amino acid, free carnitine, or an acylcarnitine, in a biological sample using tandem mass spectrometry. The resultant information (metabolic profile) can be used for assessing the health state of a subject (e.g., a human patient), such as presence or absence of a metabolic disorder (e.g., an amino acidopathy, a fatty acid or organic acid disorder, or a metabolic disorder associated with altered levels of succinylacetone (e.g., Hereditary tyrosinemia type I)), or for evaluating risk for such a disorder. Examples of amino acidopathies include, but are not limited to, argininemia, argininosuccinic aciduria (argininosuccinic lyase deficiency/argininosuccinase deficiency), citrullinemia (argininosuccinic acid synthetase deficiency/argininosuccinate synthetase deficiency), homocystinuria, cystathione synthase deficiency, hypermethioninemia, hyperomithinemia, hyperammonemia, hyperhomocitrullinuria syndrome, omithine translocase deficiency, hyperprolinemia Maple Syrup Urine Disease (branched chain ketoaciduria), nonketotic hyperglycinemia phenylketonuria, pyroglutamic/pipecolic academia, tyrosenemia (Type I), tyrosenemia (Type II), 5-oxoprolinuria, or pyroglutamic aciduria. Examples of fatty acid and organic acid disorders include, e.g., 2-methylbutyryl CoA dehydrogenase deficiency, 2,4-Dienoyl-CoA reductase deficiency, 3-hydroxy-3-methylglutaryl CoA lyase deficiency (hydroxymethylglutaric acidemia), 3-methylcrotonyl CoA carboxylase deficiency (3-methylcrotonylglycinemia), carnitine palmitoyltransferase (type I) deficiency, carnitine palmitoyltransferase (type II) deficiency, carnitine transporter defect carnitine/acylcarnitine translocase defect, ethylmalonic academia, glutaric academia (type I; glutaryl CoA dehydrogenase deficiency); isobutyryl CoA dehydrogenase deficiency Isovaleric academia, long-chain acyl-CoA dehydrogenase deficiency, long-chain hydroxyacyl-CoA dehydrogenase deficiency, malonic aciduria, medium-chain acyl-CoA dehydrogenase deficiency, methylmalonic academia, mitocondrial acetoacetyl CoA thiolase deficiency (Beta-Ketothiolase deficiency), multiple acyl-CoA dehydrogenase deficiency (Glutaric acidemia, type II), multiple Co-A carboxylase deficiency (Holocarboxylase synthetase deficiency), propionic academia, short-chain acyl-CoA dehydrogenase deficiency, short-chain hydroxyacyl-CoA dhydrogenase deficiency trifunctional protein deficiency, and very-long-chain acyl-CoA dehydrogenase deficiency. Additional metabolic disorders are described in, e.g., Chace et al. (2001) Clinical Chemistry 47:1166-82; Rashed et al. (1997) Clinical Chemistry 43(7): 1129-41; Schulze et al. (2003) Pediatrics 111(6): 1399-1406; and Zytkovicz et al. (2001) Clinical Chemistry 47(11): 1945-55.

Figure 1:
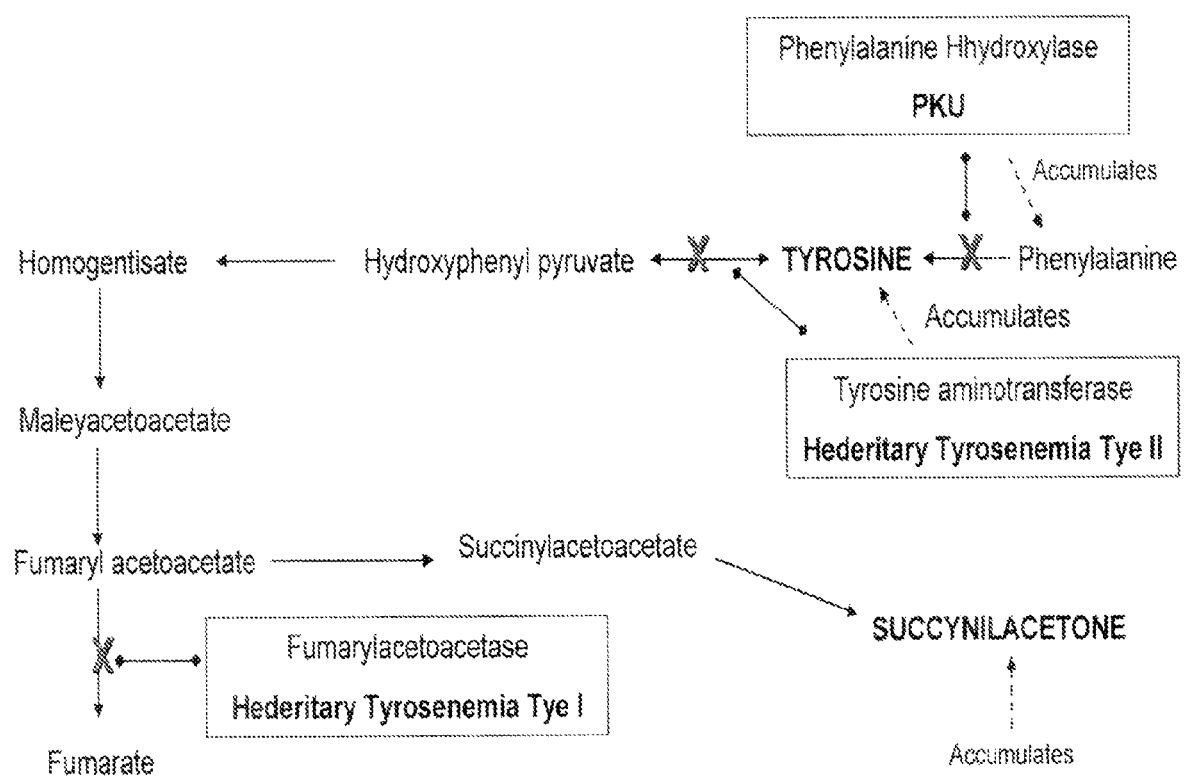
FIG. 1 is a schematic diagram depicting the pathway of tyrosine catabolism.

Tyrosinemia type I (e.g., Hereditary tyrosinemia type I), for example, is caused by the lack of fumarylacetoacetase activity which leads to the accumulation of fumarylacetoacetate (FIG. 1). Fumarylacetoacetate is rapidly converted by other enzymes to succinylacetone and thus patients with Tyrosinemia Type I accumulate succinylacetone in their blood. Therefore, the ability to detect succinylacetone either alone, or together with other biomolecules (e.g., metabolic biomolecules), can be useful for assessing the health state of a subject. Hence, it is possible to, at the same time, detect other amino acids such as tyrosine and methionine, as well and other biomolecules such as free carnitine and acylcarnitines, in the sample, e.g., by identifying unique peaks for such molecules in the mass spectrometry analysis. Table 1 includes a non-exhaustive list of analytes (e.g., biomolecules) that can be detected/measured with succinylacetone (by way of derivatized succinylacetone) using the methods described herein.

A metabolic profile obtained by the methods described herein can be used in diagnosing or predicting susceptibility to a variety of metabolic disorders because the biochemical indicators (e.g., succinylacetone) examined can be indicative of such disorders, whether or not physiologic or behavioral symptoms of the disorder have become apparent (e.g., one suspected of having a metabolic disorder such as an amino acidopathy (e.g., tyrosinemia type I). A metabolic profile as described herein can be useful for monitoring the metabolism of a subject (e.g., a mammal such as a human), such as one undergoing treatment for a metabolic disorder. As a non-limiting example, the methods can be used for determining therapeutic efficacy of a particular treatment (e.g., the ability of a treatment to restore levels of succinylacetone to physiologic levels). Based on this determination, the subject can be offered additional or alternative therapeutic options. The metabolic profile can also be useful for assessing patient compliance with a particular treatment modality, such as dietary restriction (e.g., the efficacy of a dietary regimen in restoring levels of succinylacetone to physiologic levels). Therefore, the technology described herein is applicable to screening, diagnosis, prognosis, monitoring therapy and compliance, and any other application in which determining the presence or amount of panels of two or more biomolecules, such as succinylacetone and one or more of an amino acid, free carnitine, or an acylcarnitine, is useful.

A metabolic profile generated using the methods described herein can be obtained using a variety of biological samples. Suitable samples include those described above.

In one aspect, a metabolic profile as described herein can be used to assess the presence or absence of a metabolic disorder such as an amino acidopathy (e.g., tyrosinemia type I).

Subjects of all ages can be affected by metabolic disorders diagnosed using a metabolic profile described herein. Therefore, a sample used in a method described herein can be obtained from a subject (e.g., a human) of any age, including a neonate, newborn, baby, child, and adult, such as a pregnant female and individual having or suspected of having tyrosinemia. The methods can also be used for individuals at risk of developing a metabolic disorder. Such individuals include those who have (i) a family history of (a genetic predisposition for) such disorders or (ii) one or more risk factors for developing such disorders. The methods can also be used for prenatal diagnosis if the changes in succinylacetone or at least one additional analyte (e.g., one or more of an amino acid, free carnitine, or an acylcarnitine) levels are evident in maternal samples such as amniotic fluid, maternal blood or plasma. The methods further can be used to monitor succinylacetone levels in individuals having health conditions associated with altered succinylacetone levels, such as individuals undergoing liver transplantation.

The methods described herein involve detecting the presence or amount of succinylacetone and one or more additional biological analytes (e.g., amino acids, free carnitine, or acylcarnitines, where the presence or amount of each biomolecule correlates the presence or absence of a metabolic disorder. The methods described herein can be used quantitatively, if desired, to allow comparison of test sample results with known or a pre-determined standard amount of a particular analyte(s) (e.g., by using an internal standard as described above). The methods can also be used qualitatively when a test sample is compared with a reference sample, which can be either a normal reference or metabolic disorder reference. In this format, the relative amount of biomolecules can be indicative of a metabolic disorder. A reference sample, for example, can be from a subject having, not suspected of having, or not at risk of developing a disorder such as a metabolic disorder such as an amino acidopathy (e.g., tyrosinemia type I).

Generally, a cut-off value for a given biomolecule can vary and would be known in the art for commonly tested analytes and enzymes. Routine, obvious adaptations of methods known in the art can be used to establish cut-off values for uncommonly tested analytes. A cut-off value is typically a biomolecule amount, or ratio with another biomolecule, above or below which is considered indicative of a metabolic disorder or cause for retest. Thus, in accordance with the technology described herein a reference level of at least one biomolecule in a particular sample type is identified as a cut-off value, above which there is a significant correlation between the presence of the at least one biomolecule and presence (or absence) of a metabolic disorder. It is understood that biomolecule panels can be interpreted as a whole, in parts or on an analyte-by-analyte basis.

Those of skill in the art will recognize that some cut-off values are not absolute in that clinical correlations are still significant over a range of values on either side of the cutoff; however, it is possible to select an optimal cut-off value (e.g. varying H-scores, and the like) of biomolecule for a particular sample types. Cut-off values determined for use in the methods described herein generally are compared with published ranges but can be individualized to the methodology used and patient population. It is understood that improvements in optimal cut-off values could be determined depending on the sophistication of statistical methods used and on the number and source of samples used to determine reference level values for the different biomolecules and sample types. Therefore, established cut-off values can be adjusted up or down, on the basis of periodic re-evaluations or changes in methodology or population distribution. In addition, instrument-specific cut-off values can be used, if desired, for example such as when inter-instrument performance comparability is >10%.

The reference level can be determined by a variety of methods, provided that the resulting reference level accurately provides an amount of each biomolecule above which exists a first group of subjects (e.g., humans) having a different probability of metabolic disorder than that of a second group of subjects having metabolic analyte or enzyme activity amount below the reference level. The reference level can be determined by comparison of biomolecule amount in, e.g., populations of subjects (e.g., patients) having the same metabolic disorder. This can be accomplished, for example, by histogram analysis, in which an entire cohort of patients are graphically presented, wherein a first axis represents the amount of biomolecule and a second axis represents the number of subjects in the cohort whose sample contain one or more biomolecules at a given amount. Two or more separate groups of subjects can be determined by identification of subsets populations of the cohort which have the same or similar levels of biomolecules. Determination of the reference level can then be made based on an amount which best distinguishes these separate groups. The reference level can be a single number, equally applicable to every subject, or the reference level can vary, according to specific subpopulations of subjects. For example, older subjects can have a different reference level than younger subjects for the same metabolic disorder. In addition, a subject with more advanced disease (e.g., a more advanced form of a metabolic disorder) can have a different reference value than one with a milder form of the disease.

The methods can also be used to determine the presence or amount of other biologically active ketones, e.g., steroids. For example, the methods described herein can be used to detect the presence or amount of a steroid in a biological sample obtained from a subject (e.g., a human patient), the methods can be used to diagnose, or generate metabolic profiles useful for the diagnosis, of one or more conditions associated with altered levels of steroids, e.g., 21-OH deficiency, 11b-OH deficiency, salt wasting 21-OH deficiency, adrenal cancer, adrenal hyperplasia, hypopituitarism, aldosterone synthase deficiency, adrenalcortical disorder, menopause, or pregnancy.

Methods of Identifying Compounds that Modulate Succinylacetone Levels

Also provided herein are methods of identifying compounds that modulate (e.g., decrease) the levels of succinylacetone in a cell. The compounds can modulate succinylacetone and a number of additional biological molecules such as, but not limited to, free carnitine, acylcarnitines, and amino acids (e.g., proline, methionine, or tyrosine). As discussed supra, since disregulated (e.g., elevated) levels of succinylacetone are associated with increased risk of certain disorders (e.g., amino acidopathies), compounds so identified could be useful in treating amino acidopathies such as tyrosinemia type I. Cells that can be contacted with the candidate compound can be of any species such that the cells produce succinylacetone (either synthetically or naturally). The cells can be primary cells or cell lines and can be of any histological type, e.g., without limitation, epithelial cells, fibroblasts, lymphoid cells, macrophages/monocytes, granulocytes, keratinocytes, neuronal cells, or muscle cells. The cells can be cultured in tissue culture dishes. Often it is preferable to grow the cells in multiwell assay plates (e.g., 96 well or 384 well assay plates) such that multiple candidate compounds can be evaluated at one time. The candidate compound (optionally at various concentrations ranging, e.g., from 0.001 nM to 10 mM) can be added to a solution (e.g., culture medium) containing the cells or, where the compound is a protein, the cells can recombinantly express it. Following incubation of cells expressing succinylacetone, the presence or level of succinylacetone can be determined using the sample preparation (extraction) and tandem mass spectrometry methods described herein. Prior to detection, the cells can be lysed under conditions that allow for a sample to be prepared, which is compatible with the extraction methods described herein and with tandem mass spectrometry. Often a control compound can be added to a set of cells as either a positive or negative control.

The compounds identified in any of the methods described herein include various chemical classes. Compounds can be biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs. Compounds can be both small or large molecule compounds.

Identification of test compounds through the use of the various libraries described herein permits subsequent modification of the test compound "hit" or "lead" to optimize the capacity of the "hit" or "lead" to modulate the levels of succinylacetone in a cell.

The methods described herein can be modified to identify compounds that modulate the levels of a biologically active ketone, e.g., a steroid or any of the biologically active ketones described herein.

Kits

Also provided herein are kits useful for preparing samples for detection and/or measurement (using tandem mass spectrometry) of succinylacetone along with multiple other analytes (e.g., amino acids, free carnitine, and acylcarnitine) in a sample, e.g., a dried blood sample or any of the samples described herein. The kits can be used to extract succinylacetone along with one or more additional analytes (e.g., amino acids, acylcarnitines, and carnitines) from a sample (e.g., a blood spot) in a single step such that the concentrations of succinylacetone and additional analytes (e.g., amino acids, carnitine, and acylcarnitines) in the extract reflect their respective concentrations (or ratios) in the sample. The kits can be used to prepare a sample to simultaneously screen succinylacetone, alanine, arginine, citrulline, glycine, leucine, methionine, ornithine, phenylalanine, proline, tyrosine, valine, and acylcarnitines such as CO, C2, C3, C3DC/C4OH, C4, C4DC/C5OH, C5, C5:1. C5DC/C6OH, C6, C6DC/C7OH, C8, C8:1, C10, C10:1, C10:2, C12, C12:1, C14, C14:1, C14:2, C14OH, C16, C16:1, C16OH, C16:10H, C18, C18:1, C18:2, C18OH, C18:1OH (see Table 1).

The kits can include one or more internal standards and/or controls for use in subsequent mass spectrometric analysis. For example, the kits can include succinylacetone (SA) as a control and a derivatized form of labeled (e.g., isotope labeled) SA (e.g., $3,4,5,6,7-{}^{13}C_5$-(3-(5-methyl-1H-pyrazol-3-yl)propionic acid (MPP)) as an internal standard. The succinylacetone and/or derivatized succinylacetone can each be provided in the kit in a liquid or dried (e.g., lyophilized) form. The succinylactone and/or derivatized succinylacetone can be provided in an amount of about 1 mmole (e.g., about 1.5 mmole, about 2 mmole, about 2.5 mmole, about 3.0 mmole, about 3.5 mmole, about 4.0 mmole, about 4.5 mmole, or about 5 mmole). The kits can include succinylacetone or derivatized succinylacetone (e.g., MPP) in a container containing one or more additional controls or internal standards. For example, the kit can include a container with a succinylacetone control, one or more amino acid controls, and one or more carnitine (e.g., free carnitine and acylcarnitines) controls. The kits can also include proline as a control and stable, labeled (e.g., isotope-labeled) proline as an internal standard.

The kits can also include a strong base such as hydrazine, e.g., hydrazine dihydrochloride or any of the other strong bases described herein. The base can be provided in solution at a concentration of less than about 0.5% (e.g., less an about 0.05%, less than about 0.06%, less than about 0.07%, less than about 0.08%, less than about 0.09%, less than about 0.1%, less than about 0.15%, less than about 0.2%, less than about 0.25%, less than about 0.3%, less than about 0.35%, less than about 0.4%, less than about 0.45%, or less than about 0.475%).

One or more solutions contained in the kit can be stored in, e.g., silanized glass vials. One or more components of the kit can be stored in a container that prevents or minimizes loss of material or evaporation of a solvent. For example, the container can be sealed with a septum.

The kits can include, e.g., dried blood (e.g., plasma, lymph) spots useful as a control. For example, the dried blood spot can be enriched with one or more analytes (e.g., one or more analytes at known concentrations) such as succinylacetone, one or more amino acids, free carnitine, or one or more acylcarnitines.

The kits can also, optionally, include an extraction solution such as any of the extraction solutions described herein. The extraction solution can contain a C1-3 linear or branched monoalcohol and a strong base. The kits can also include one or more solvent solutions containing, e.g., acetonitrile or isopropanol. The solvent solutions can also contain water, e.g., a solvent solution containing 80% acetonitrile and 20% water.

In some embodiments, the kit can also include one or more components to test for biotinidase activity in a sample as well as to test for the presence of lysosomal storage disorders or galactosemia in a subject.

Such kits can be used then in the detection of elevated or low succinylacetone, amino acids, free carnitine, or acylcarnitine levels in newborn blood for the diagnosis of one or more of several metabolic disorders. For example, elevated levels of succinylacetone can be indicative of tyrosinemia type I. Free carnitine and acylcarnitines are markers for disorders that are generally classified as fatty acid oxidation (FAO) disorders and organic aciduria disorders (OAD). Similarly, amino acids are used as markers for several metabolic disorders collectively known as amino acidopathies. These disorders are inborn errors of metabolism (or genetic metabolic deficiencies).

It is understood that modifications that do not substantially affect the activity of the various embodiments of this invention are also included within the definition of the invention provided herein. Accordingly, the following example is intended to illustrate, not to limit, the present invention.

EXAMPLES

Example 1

Reference standard blood (whole blood) spots were prepared using whole blood obtained from a subject. The blood was processed by adjusting the hemoglobin concentration to 17 mg/dL and adding to the blood several amino acids, carnitine, acylcarnitines and succinylacetone at known concentrations. The processed blood was dispensed onto filter paper cards to form blood spots on the filter paper matrix. Each blood spot was generated by dispensing 75 μL of processed blood. The blood spots were allowed to dry overnight.

A small disc (⅛") of a dried blood spot was punched and deposited in a well of a micro titer plate well. The sample was extracted by dispensing 100 μL of an extraction solution that consisted of a mixture of methanol and water at an approximate relative volume-to-volume ratio of 78% methanol and 22% water. In addition, the extraction solution contained a 3 mM oxalic acid, and a concentration of 600 μM of hydrazine dihydrochloride. Internal standards (stable heavy isotope analogs of the analytes of interest) for several amino acids, carnitine, acylcarnitines, and succinylacetone (MPP) were also present in the extraction solution. The internal standards included in the solution are indicated in tandem mass spectrometry scan shown in FIG. 5.

The extracted sample was injected into an electrospray triple quadrupole tandem mass spectrometer with the aid of an automated liquid handling device. Mass spectral data for the amino acids and succinylacetone (MPP) were acquired via a neutral loss of 46 scan (FIG. 5).

Example 2

Blood spots containing several amino acids, carnitine, acylcarnitines, and succinylacetone at known concentrations were prepared as above (Example 1). A small disc (⅛") of a dried blood spot was punched and deposited in a well of a micro titer plate well. The sample was extracted in the presence of internal standards as described above.

Following extraction, the sample was evaporated to dryness. The dried sample was then reconstituted in 3N HCl in n-butanol and incubated at 39° C. for about 30 minutes. Following this incubation, the sample was again evaporated to dryness and then reconstituted in a solution of acetonitrile and water.

Figure 6:
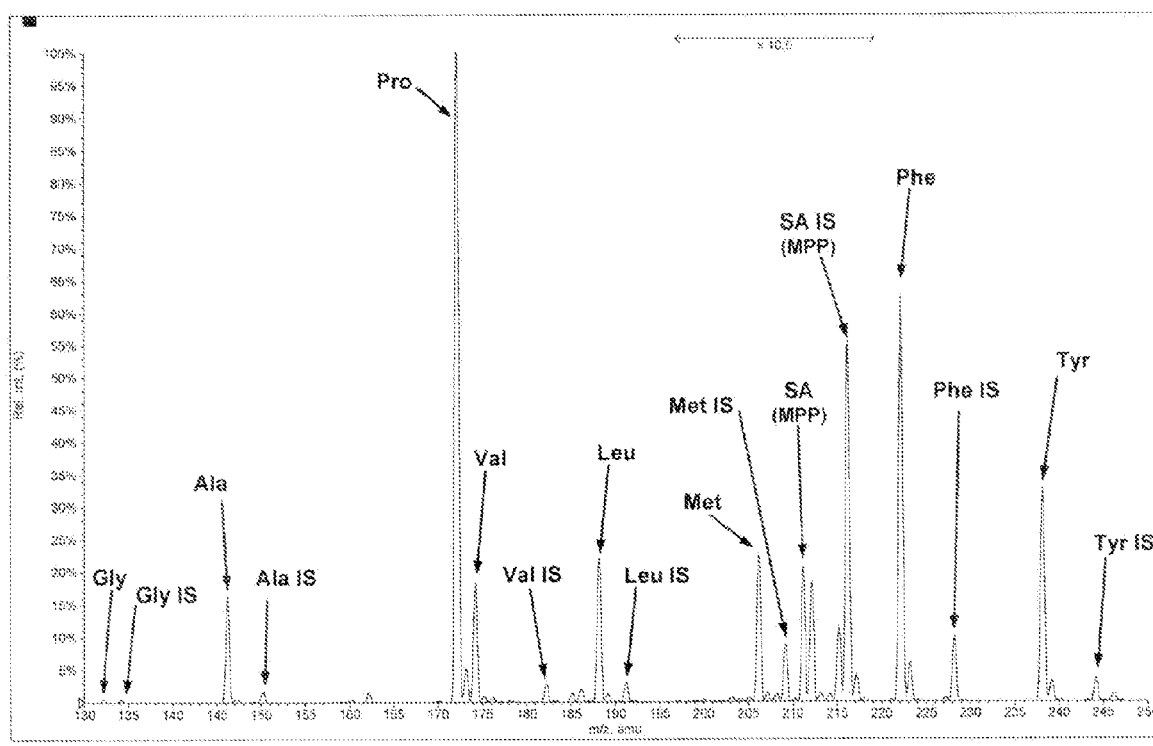
FIG. 6 is a tandem mass spectrum (Neutral loss of 102 scan) of an extracted blood spot depicting exemplary analytes that can be detected and/or measured together with succinylacetone when the sample is processed according to the method depicted in FIG. 4.

The extracted sample was injected into an electrospray triple quadrupole tandem mass spectrometer with the aid of an automated liquid handling device. The data was acquired in the neutral loss of 102 scan. The formation of butyl esters is evident by the 56 dalton (Da) increase (cross reference FIG. 5) in the m/z of the tons brought about by this esterification (FIG. 6). These data demonstrate that following the derivatization of succinylacetone (as described herein), the sample can be further processed (e.g., by esterification), if need be, to detect other analyte constituents.

Example 3

Dried blood spots were prepared as above. The blood spots were spiked with different levels of the analytes (amino acids, Succinylacetone (SA), free carnitine and acylcarnitines) shown in Table 2 and Table 3. The blood spots were extracted as described above (Example 1; the definition for each of the analytes indicated in the tables can be found in Table 1.) The extracted sample was injected into an electrospray triple quadrupole tandem mass spectrometer with the aid of an automated liquid handling device. The mass spectral data for the amino acid and succinylacetone (MPP) was acquired via a neutral loss of m/z 46 scan and for carnitine and acylcarnitines via a precursor ion of m/s 85 scan. The percentage of each analyte recovered was determined through comparison with an internal standard for each analyte.

The various recoveries, by percentage, are presented in Table 2 the various levels of precision are presented in Table 3.

The imprecision of the assay was determined by analyzing the samples described in table three. Each sample run consisted of triplicate punches of each sample which were processed and measured as described in Example 1. The study included two such runs a day for a total of five days. With this information the following imprecision components were determined: within run, between run-within day, and between day from which the total imprecision was determined. The results of the imprecision analysts are shown in Table 3.

These data demonstrate that the methods described herein can be used to simultaneously extract and quantify MPP, amino acids, carnitine and acylcarnitines using tandem mass spectrometry.

Example 4

Tyrosine is currently used as a diagnostic marker for screening tyrosinemia type I. To show that detection of succinylacetone, as compared to tyrosine, results in an increase in specificity for determining tyrosinemia type I status in an individual, blood samples from an affected patient (i.e., tyrosinemia type I positive patient) were compared to known normal samples for the corresponding tyrosine and succinylacetone (MPP) concentrations. Dried blood spots from healthy newborns and from a newborn with a confirmed case of tyrosinemia type I were obtained at 25 hours and 14 days of age. The blood spots were extracted and subjected to mass spectrometric analysis as described above (Example 1).

Figure 7:
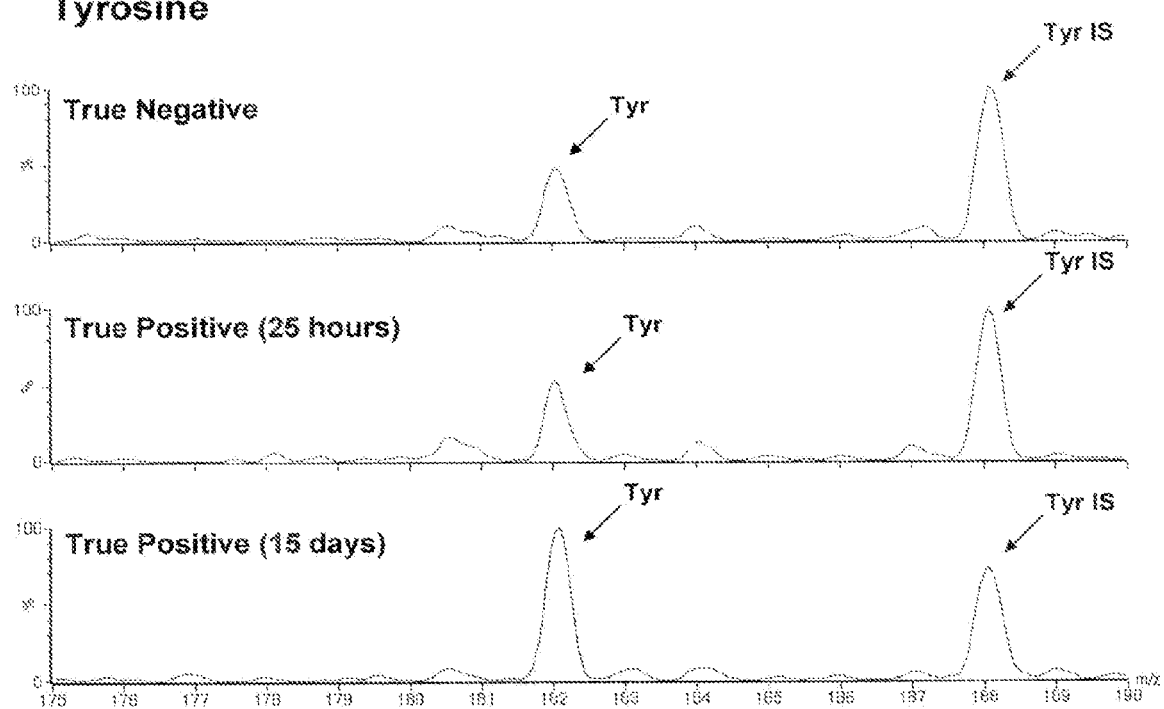
FIG. 7 is a series of spectra (Neutral loss of 46 scan) acquired with the method described in FIG. 3. The spectra depict the measurement of succinylacetone and tyrosine levels in dried blood spots from healthy newborns and from a newborn confirmed as having tyrosinemia type I. The X-axis represents the corresponding m/z and the peaks heights represent the relative abundance of the analytes.
Figure 7:
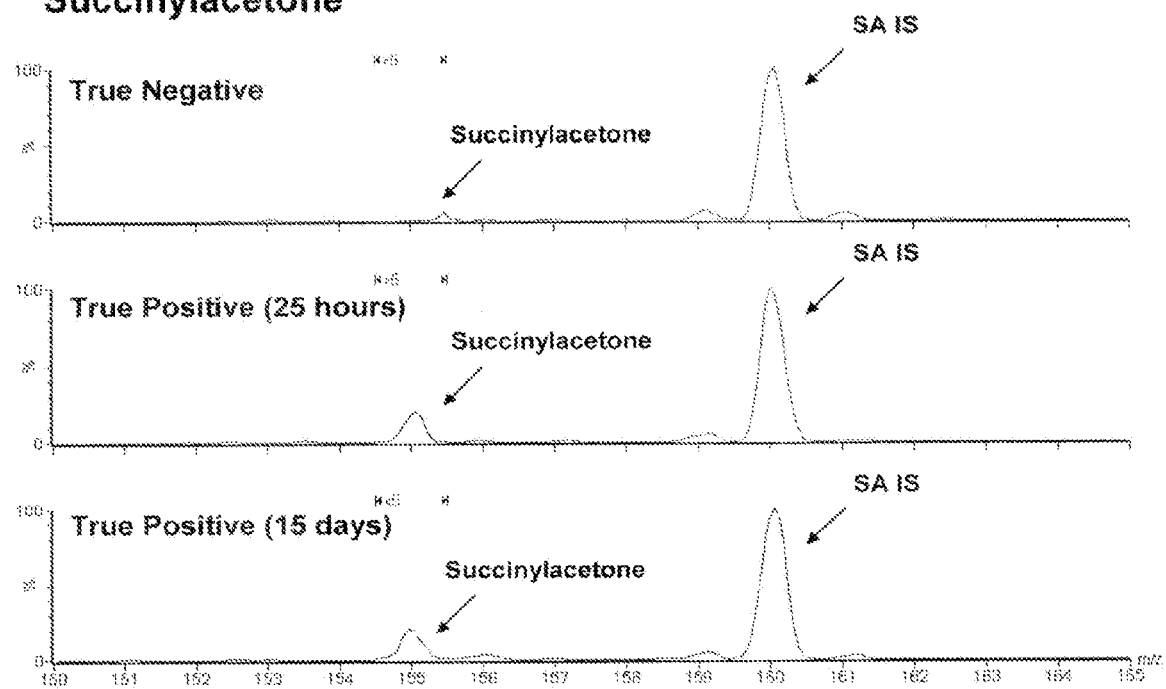
Figure 8:
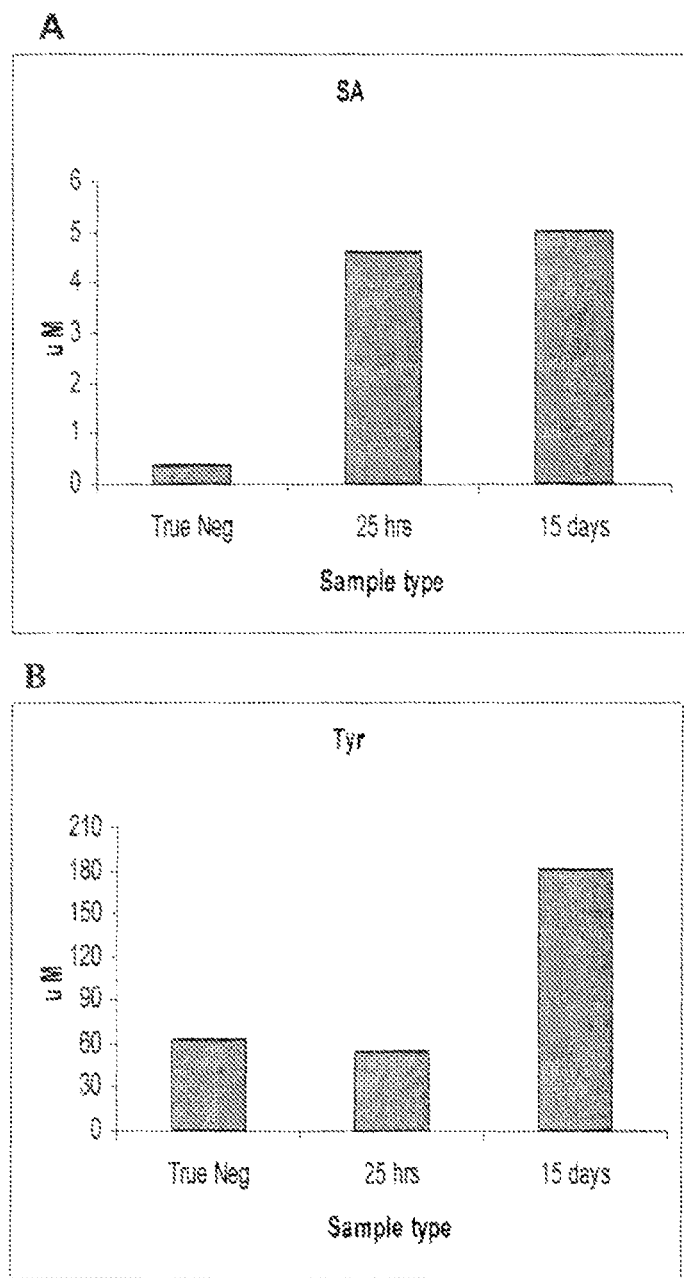
FIG. 8 are a pair of bar graphs and a table depicting the measurement of succinylacetone and tyrosine levels in dried blood spots obtained from a newborn continued as having tyrosinemia type I at 25 hours and 15 days, as compared to a healthy newborn ("true neg"). The Y-axis of the bar graph of FIG. 8A represents the level of succinylacetone in μM (left). The Y-axis of the bar graph of FIG. 8B represents the level of tyrosine in μM (right).

Although the affected patient displays normal tyrosine levels at 25 hours of age (the newborn screening window), it is not until the patient is 14 days old that the tyrosine levels are significantly elevated (FIG. 7 spectra and FIG. 8; table and bar graphs). In contrast, succinylacetone (MPP) shows very significant elevation (30-40 standard deviations form the normal mean) even as early as 25 hrs after birth. Thus, at 25 hrs of age, this patient would have been a false negative if tyrosine would have been the only marker used. Since early detection is crucial for tyrosinemia type I, detecting succinylacetone is very advantageous for diagnosing this condition.

Example 6

Figure 9:
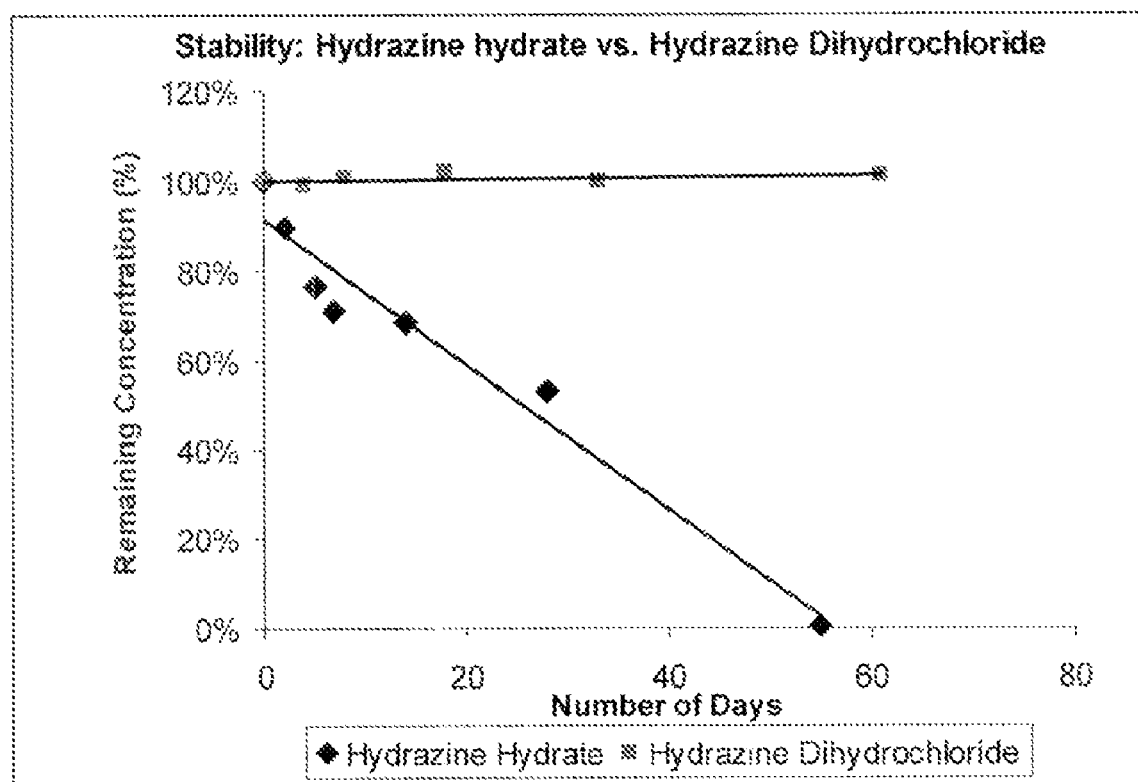
FIG. 9 is a line graph depicting the relative stability of hydrazine hydrate and hydrazine dihydrochloride. The X-axis represents the number of days and the Y-axis represents the amount (percentage) of hydrazine hydrate (diamonds) or hydrazine dihydrochloride (squares) remaining at each time point.

Many of the methods described herein use a strong base to form a Schiff base with succinylacetone so it can be extracted and measured. Hydrazine can be obtained in several forms, e.g., hydrazine hydrate or hydrazine dihydrochloride. Although both of these forms perform similarly in the methods described herein, to test which of the two forms of hydrazine are the most stable, and thus would have the longest shell-life, the relative stability of each form was tested over a time span about 60 days. Solutions of each form of hydrazine (hydrazine hydrate at 0.5% and hydrazine dihydrochloride at 0.1%) were incubated at 30° C. and at various time points (e.g., 1 to about 60 days), the amount of each hydrazine form was determined by a standardized fluorometric assay. Hydrazine hydrate was determined to be unstable, whereas, hydrazine dihydrochloride was determined to be much more stable and thus much more suitable for a robust product (FIG. 9).

TABLE 2

Percent recoveries for various analytes in dried blood.

|  | ALA | ARG | CIT | GLY | LEU | MET | SA | ORN | PHE | PRO | TYR | VAL |
|---|---|---|---|---|---|---|---|---|---|---|---|---|
| Spike (μM) | 81 | 79 | 31 | 83 | 45 | 21 | 4 | 68 | 42 | 63 | 54 | 41 |
| Recovery | 67 | 70 | 90 | 83 | 68 | 74 | 72 | 100 | 101 | 96 | 94 | 78 |
| Spike (μM) | 644 | 635 | 251 | 665 | 357 | 171 | 29 | 544 | 337 | 507 | 431 | 324 |
| Recovery | 77 | 71 | 86 | 79 | 70 | 73 | 69 | 94 | 99 | 94 | 93 | 83 |
| Spike (μM) | 1450 | 1429 | 564 | 1495 | 803 | 385 | 65 | 1223 | 759 | 1141 | 969 | 730 |
| Recovery | 78 | 71 | 83 | 78 | 70 | 72 | 66 | 92 | 99 | 92 | 91 | 83 |
| Spike (μM) | 3261 | 3216 | 1270 | 3364 | 1807 | 866 | 147 | 2752 | 1708 | 2567 | 2181 | 1642 |
| Recovery | 90 | 80 | 92 | 88 | 79 | 81 | 76 | 101 | 109 | 104 | 102 | 93 |

|  | C0 | C2 | C3 | C4 | C5 | C5DC | C6 | C8 | C10 | C12 | C14 | C16 | C18 |
|---|---|---|---|---|---|---|---|---|---|---|---|---|---|
| Spike (μM) | 45 | 14 | 1.7 | 1.3 | 1.2 | 0.5 | 1.2 | 0.8 | 0.5 | 0.9 | 0.8 | 1.5 | 0.5 |
| Recovery | 101 | 79 | 72 | 71 | 80 | 102 | 83 | 80 | 85 | 82 | 87 | 84 | 90 |
| Spike (μM) | 362 | 110 | 14 | 10 | 10 | 4 | 10 | 7 | 4 | 7 | 6 | 12 | 4 |
| Recovery | 94 | 77 | 73 | 68 | 76 | 97 | 80 | 76 | 80 | 78 | 84 | 82 | 79 |
| Spike (μM) | 814 | 248 | 31 | 24 | 21 | 9 | 21 | 15 | 9 | 15 | 14 | 28 | 10 |
| Recovery | 92 | 75 | 71 | 66 | 74 | 95 | 77 | 73 | 78 | 75 | 83 | 81 | 80 |
| Spike (μM) | 1831 | 557 | 70 | 53 | 48 | 21 | 48 | 33 | 20 | 35 | 31 | 62 | 22 |
| Recovery | 102 | 83 | 81 | 75 | 82 | 104 | 87 | 80 | 88 | 85 | 92 | 90 | 88 |

$$\text{Percent recovery} = \frac{\text{(measured concentration)} - \text{(endogenous concentration)}}{\text{Spiked concentration}} \times 100$$

TABLE 3

Total imprecision.

|  | ALA | ARG | CIT | GLY | LEU | MET | SA | ORN | PHE | PRO | TYR | VAL | C0 |
|---|---|---|---|---|---|---|---|---|---|---|---|---|---|
| Measured μM | 567.1 | 30.0 | 29.1 | 327.7 | 185.6 | 27.2 | 0.8 | 127.2 | 84.7 | 275.5 | 83.8 | 206.2 | 51.0 |
| % CV | 8 | 7 | 11 | 10 | 7 | 7 | 25 | 7 | 7 | 9 | 8 | 8 | 7 |
| Measured μM | 604.1 | 51.1 | 39.7 | 359.0 | 201.2 | 33.5 | 1.7 | 152.5 | 102.2 | 304.4 | 104.1 | 222.9 | 67.9 |
| % CV | 9 | 7 | 10 | 9 | 7 | 8 | 21 | 7 | 8 | 9 | 7 | 8 | 7 |
| Measured μM | 709.9 | 135.6 | 81.6 | 463.1 | 251.8 | 57.0 | 5.4 | 254.6 | 166.3 | 398.9 | 182.0 | 278.6 | 134.9 |
| % CV | 8 | 6 | 8 | 8 | 6 | 7 | 12 | 6 | 7 | 6 | 7 | 7 | 8 |
| Measured μM | 1104.2 | 476.8 | 243.9 | 867.0 | 447.1 | 152.3 | 20.5 | 637.2 | 419.5 | 763.4 | 482.8 | 489.2 | 390.0 |
| % CV | 7 | 7 | 9 | 9 | 6 | 7 | 10 | 7 | 8 | 9 | 7 | 8 | 6 |

|  | C2 | C3 | C4 | C5 | C5DC | C6 | C8 | C10 | C12 | C14 | C16 | C18 |
|---|---|---|---|---|---|---|---|---|---|---|---|---|
| Measured μM | 36.4 | 3.3 | 0.3 | 0.3 | 0.2 | 0.1 | 0.1 | 0.1 | 0.1 | 0.2 | 2.2 | 2.1 |
| % CV | 7 | 9 | 11 | 11 | 13 | 12 | 13 | 12 | 10 | 10 | 8 | 7 |
| Measured μM | 42.0 | 4.0 | 0.7 | 0.6 | 0.4 | 0.5 | 0.4 | 0.3 | 0.4 | 0.4 | 2.7 | 2.3 |
| % CV | 8 | 11 | 10 | 10 | 12 | 10 | 9 | 10 | 8 | 8 | 7 | 6 |
| Measured μM | 60.8 | 6.3 | 2.2 | 2.0 | 1.2 | 2.0 | 1.3 | 0.9 | 1.5 | 1.4 | 4.6 | 2.9 |
| % CV | 7 | 8 | 8 | 7 | 10 | 8 | 8 | 9 | 7 | 7 | 6 | 6 |
| Measured μM | 134.6 | 15.3 | 8.3 | 7.4 | 4.2 | 7.7 | 5.0 | 3.3 | 6.0 | 5.3 | 12.2 | 5.5 |
| % CV | 7 | 9 | 10 | 7 | 8 | 8 | 7 | 7 | 7 | 7 | 8 | 10 |

Total % CV includes: within run, between run - within day, and between day imprecision.

Other embodiments are within the scope of the following claims.

What is claimed is:

1. A method for detecting succinylacetone, the method comprising:
 contacting a sample with an extraction solution comprising methanol and a strong base;
 derivatizing succinylacetone in the sample; and
 evaluating the derivatized succinylacetone in the derivatized sample using tandem mass spectrometry.

2. A method for detecting succinylacetone, the method comprising:
 contacting a sample with an extraction solution comprising methanol and hydrazine;
 derivatizing succinylacetone to 3-(5-methyl-1H-pyrazol-3-yl) propionic acid (MPP) in the sample; and
 evaluating MPP in the derivatized sample using tandem mass spectrometry.

3. The method of claim 2, further comprising evaluating the sample for one or more additional analytes.

4. The method of claim 3, wherein the one or more additional analytes are evaluated with MPP in the same sample injection.

5. A method for detecting succinylacetone, the method comprising:
 contacting a sample with an extraction solution containing an organic solvent under conditions that do not substantially fix proteins;
 derivatizing succinylacetone to 3-(5-methyl-1H-pyrazol-3-yl) propionic acid (MPP) in the sample; and
 evaluating MPP and an additional analyte (or derivative thereof) in the derivatized sample using tandem mass spectrometry.

6. The method of claim 2 or 5, wherein the extraction solution comprises at least about 5% water.

7. The method of claim 2 or 5, wherein the extraction solution comprises less than about 85% methanol.

8. The method of claim 2 or 5, wherein the succinylacetone is derivatized with hydrazine or derivatized hydrazine.

9. The method of claim 2 or 5, wherein the sample is a dried blood sample.

10. The method of claim 2 or 5, wherein the sample is from a newborn human.

11. The method of claim 2 or 5, further comprising determining whether a subject, from whom the sample was derived, has, or is at risk of developing, hereditary tyrosinemia type I, based on the detection of succinylacetone in the sample.

12. The method of claim 11, further comprising after determining that the subject has, or is at risk of developing, hereditary tyrosinemia type I, administering to the subject an inhibitor of 4-hydroxyphenylpyruvate dioxygenase.

13. The method of claim 2 or 5, wherein a derivatized succinylacetone comprising at least one heavy atom isotope is included in the sample prior to mass spectroscopic analysis.

14. A method for detecting a biologically active ketone, the method comprising:
 contacting a sample with an extraction solution comprising methanol and a strong base;
 derivatizing a biologically active ketone in the sample; and
 evaluating the derivatized biologically active ketone in the derivatized sample using tandem mass spectrometry.

15. The method of claim 14, wherein the biologically active ketone is succinylacetone.

16. The method of claim 14, wherein the biologically active ketone is a steroid.

17. A kit for detecting succinylacetone, the kit comprising:
 derivatized succinylacetone comprising at least one heavy atom isotope;
 an extraction solution comprising methanol and a strong base; and
 instructions for how to detect the derivatized succinylacetone.

18. The kit of claim 17, wherein the derivatized succinylacetone is 3-(5-methyl-1H-pyrazol-3-yl) propionic acid (MPP).

19. The kit of claim 17, wherein the strong base is hydrazine.

20. The kit of claim 19, wherein the hydrazine is hydrazine dihydro chloride.

21. The kit of claim 19, wherein the hydrazine is in solution at a concentration of less than about 0.1%.

22. The kit of claim 17, further comprising one or more internal standards, each internal standard comprising: (i) an amino acid, free carnitine, or an acylcarnitine and (i) at least one heavy atom isotope.

23. The kit of claim 17, further comprising at least one dried blood spot comprising a known amount of one or more of succinylacetone, an amino acid, free carnitine, or an acylcarnitine.

24. A method for extraction, the method comprising:
 contacting a sample with an extraction solution, the extraction solution comprising methanol and a strong base, wherein contacting the sample with the extraction solution yields an extract comprising (i) derivatized succinylacetone, (ii) one or more amino acids, (iii) free carnitine, (iv) one or more acylcarnitines or (v) a derivatized form of (ii), (iii), or (iv) from the sample, wherein the concentration of the derivatized succinylacetone if present in the extract reflects the concentration of succinylacetone in the sample, and wherein the concentrations of the one or more amino acids, free carnitine, one or more acylcarnitines, or derivatized forms thereof if present in the extract reflect their respective concentrations in the sample.

25. The method of claim 24, further comprising after contacting the sample with the extraction solution, analyzing the sample using tandem mass spectrometry.

26. The method of claim 24, wherein the contacting derivatizes at least one succinylacetone molecule to 3-(5-methyl-1H-pyrazol-3-yl) propionic acid (MPP).

27. The method of claim 24, wherein the sample is a biological sample.

28. The method of claim 27, wherein the biological sample is a dried blood sample.

29. The method of claim 24, wherein the extraction solution further comprises water.

30. The method of claim 24, wherein the extraction solution comprises between about 5% to about 30% water.

31. The method of claim 24, wherein the strong base is hydrazine.

32. The method of claim 24, wherein the strong base is a modified hydrazine.

33. The method of claim 24, wherein the extraction solution further comprises an organic acid.

34. The method of claim 33, wherein the organic acid is oxalic acid.

35. The method of claim 24, wherein the extraction solution further comprises one or more internal standards.

36. The method of claim 24, further comprising after contacting the sample with the extraction solution, evaporating the sample resulting in a first evaporated sample.

37. The method of claim 36, further comprising after evaporating the sample, contacting the first evaporated sample with an alkyl alcohol solution comprising an alkyl alcohol and an acid.

38. The method of claim 37, wherein the alkyl alcohol is n-butanol.

39. The method of claim 37, wherein the acid is HCl.

40. The method of claim 37, further comprising after contacting the sample with the alkyl alcohol solution, evaporating the solution resulting in a second evaporated sample.

41. The method of claim 40, further comprising reconstituting the second evaporated sample.

42. The method of claim 41, wherein reconstituting comprises contacting the second evaporated sample with a solvent comprising acetonitrile.

* * * * *

UNITED STATES PATENT AND TRADEMARK OFFICE
CERTIFICATE OF CORRECTION

| | | |
|---|---|---|
| PATENT NO. | : 7,951,608 B2 | Page 1 of 1 |
| APPLICATION NO. | : 11/744789 | |
| DATED | : May 31, 2011 | |
| INVENTOR(S) | : Cerda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 754 days.

Signed and Sealed this
Twentieth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,951,608 B2 | Page 1 of 1 |
| APPLICATION NO. | : 11/744789 | |
| DATED | : May 31, 2011 | |
| INVENTOR(S) | : Cerda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 780 days.

Signed and Sealed this
Sixth Day of November, 2012

David J. Kappos
*Director of the United States Patent and Trademark Office*